United States Patent [19]
Umber et al.

[11] Patent Number: 5,257,995
[45] Date of Patent: Nov. 2, 1993

[54] APPARATUS FOR REMOVING A PROSTHESIS FROM A BONE

[75] Inventors: Ray E. Umber, Arlington; William J. Vaughn, Fort Worth, both of Tex.

[73] Assignee: Midas Rex Pneumatic Tools, Inc., Fort Worth, Tex.

[21] Appl. No.: 851,048

[22] Filed: Mar. 13, 1992

[51] Int. Cl.⁵ ............................................. A61F 2/32
[52] U.S. Cl. ..................................... 606/99; 606/86; 606/96
[58] Field of Search ................... 606/79, 80, 86, 96, 606/99; 623/16, 18, 23

[56] References Cited

U.S. PATENT DOCUMENTS 4,399,813  8/1983  Barber ................................. 606/99

FOREIGN PATENT DOCUMENTS 3538654  4/1987  Fed. Rep. of Germany ........ 606/80
2166357A  5/1986  United Kingdom ................. 606/80

Primary Examiner—David Isabella
Attorney, Agent, or Firm—James E. Bradley

[57] ABSTRACT

A dissecting device assists in removing a prosthesis from an embedded engagement within a bone. The device includes a cutting tool having a cutting tip and an elongated shank which has a diameter and length selected so as to allow significant lateral flexing. A motor configured to be gripped by one hand of a user, is connected to the cutting tool shank for providing rotational motion to the cutting tool. A handle configured to gripped by another hand of the user has a bearing carrier having a hole therethrough which rotatably receives the shank. The user will move the motor and the handle to guide the cutting tool around the perimeter of the prosthesis to dissect a thin layer between the prosthesis and the bone to release the prosthesis from the bone.

7 Claims, 2 Drawing Sheets

APPARATUS FOR REMOVING A PROSTHESIS FROM A BONE

BACKGROUND OF THE INVENTION

1. Field of the Invention:

This invention relates in general to high speed cutting tool equipment for human bone surgery, and in particular to an apparatus for removing a prosthesis from an embedded engagement within a bone.

2. Description of the Prior Art:

In orthopedic surgery, occasions arise when a prosthesis previously installed must be removed. Possibly the bone has broken, the prosthesis become damaged, or an infection has occurred. The prosthesis normally will be a metal member that has been inserted within a hole drilled in a bone. The prosthesis may be held by an adhesive, or also by ingrowth of the bone around the prosthesis.

Removing the prosthesis can be a difficult task. One particular problem is in removing a porous coated prosthesis from the femur hip joint. This prosthesis has a rough exterior which enhances growth of the bone around the prosthesis. The prosthesis may be embedded from two to six inches in the bone. Typically, the surgeon utilizes an osteotome, which is essentially a chisel. The chisel wedges between the bone and the prosthesis. The surgeon works around the prosthesis to provide a clearance, separating the prosthesis from the bone so that it can be pulled out. The wedging action may cause splintering of the bone. It is also time consuming.

SUMMARY OF THE INVENTION

An apparatus is provided for removing a prosthesis by using a rotary motor of a type conventionally used for resecting, drilling and performing other cutting actions on bone. In this apparatus, the cutting tool has a cutting tip and an elongated flexible shank. The shank is capable of flexing laterally a significant degree.

A guide has a handle for holding by the user. The guide has a hole through it which rotatably receives the shank of the cutting tool. The user holds the motor in one hand and the guide in the other hand while operating the cutting tool. The guide will be used to guide the cutting tip around the perimeter of the prosthesis. This resects a thin layer between the prosthesis and the bone to release the prosthesis from the bone.

DESCRIPTION OF THE INVENTION

Figure 1:
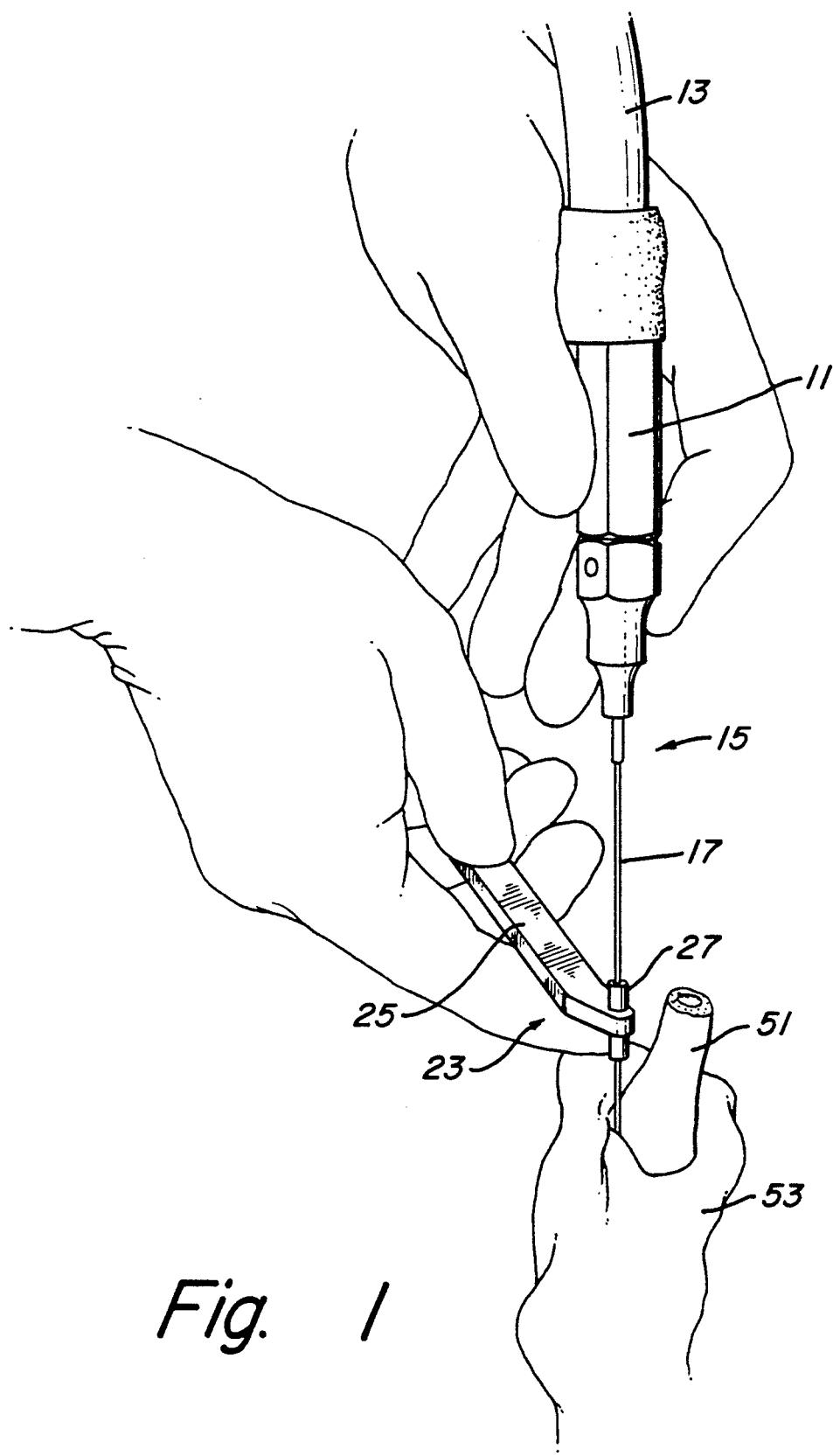
FIG. 1 is a perspective view illustrating an apparatus constructed in accordance with this invention, shown in use.

Referring to FIG. 1, a motor 11 is employed in this apparatus and method. Motor 11 is a conventional, high speed air driven motor for use in orthopedic surgery. Motor 11 is commercially available and has a rotational speed of about 73,000 rpm when not under load. An air hose 13 supplies air to drive motor 11 for rotating a chuck or collet (not shown) which grasps a cutting tool 15.

Figure 5:
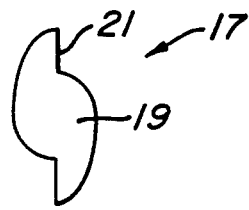
FIG. 5 is a sectional view of a lower portion of the tip of the cutting tool used with the apparatus of FIG. 1.

Cutting tool 15 is conventional, except it may be longer than normally employed in orthopedic surgery. Cutting tool 15 has a cylindrical shank 17 terminating in a tip 19 (FIG. 5). The upper end of shank 17 is 16 larger in diameter for clamping in the collet of motor 11. Tip 19 may be of various configurations. In FIG. 5, it is shown to be of a type having a pair of flutes 21 on opposite sides. Flutes extend up a short distance from the lower end of tip 19 to perform cutting action.

Shank 17 is thin, and although made of high speed steel, is laterally flexible. It is capable of bending a significant degree, such as up to 45 degrees, without permanent deformation. Shank 17 may be of various diameters, preferably being from about 1.2 mm to 1.5 mm. Shank 17 is preferably about ten inches in length, although it may be shorter.

A guide 23 is employed to guide shank 17 during dissecting operations. Guide 23 has a handle 25 that extends laterally from shank 17. Handle 25 is a flat member about six inches in length for gripping by a hand of a user. Handle 25 has on one end a bearing carrier 27 through which shank 17 will pass.

Figure 2:
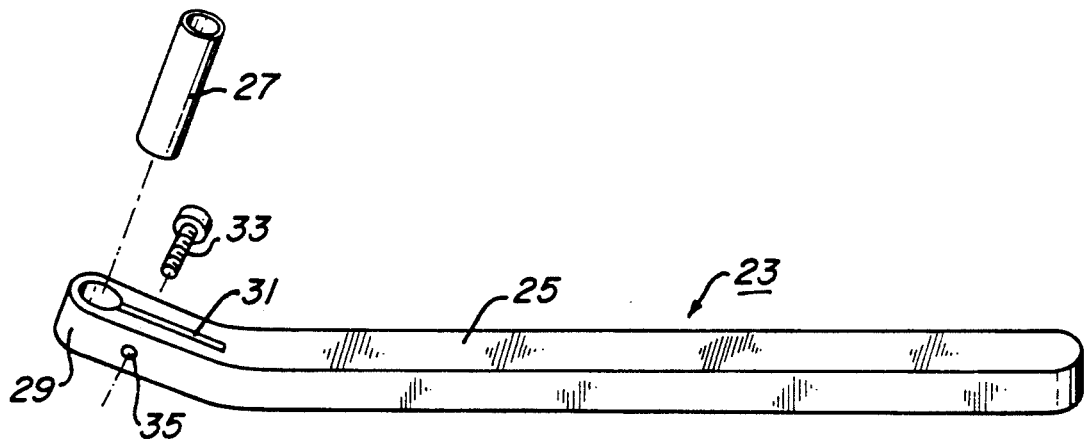
FIG. 2 is a perspective view of the guide used with the apparatus of Figure showing the bearing carrier and screw in exploded form.

Referring to FIG. 2, bearing carrier 27 mounts releasably to handle 25 so that it can be removed for replacement if worn. Bearing carrier 27 mounts within a pair of semicircular jaws 29 integrally formed on one end of handle 25. Jaws 29 will deflect toward each other to frictionally grip bearing carrier 27. A slot 31 extends rearward from jaws 29 so as to allow jaws 29 to be flexed inward to grip bearing carrier 27. A screw 33 extends across slot 31, engaging a hole 35 on the opposite side to deflect jaws 29 inward to grip bearing carrier 27, or to release jaws 29 to remove bearing carrier 27. The end of handle 25 that contains jaws 29 inclines relative to the remaining portions of handle 25, preferably at about a 160 degree angle relative to the remaining portions of handle 25.

Figure 3:
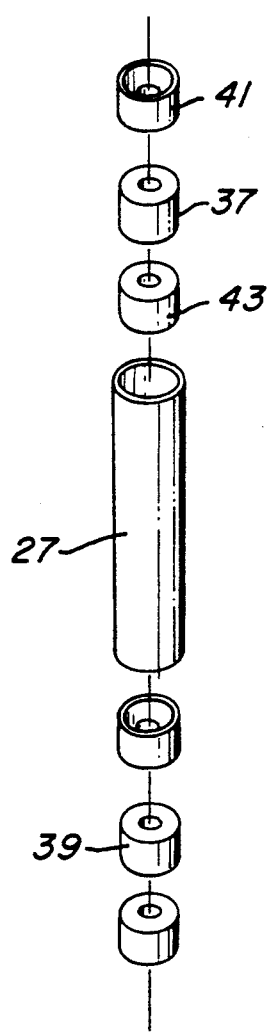
FIG. 3 is an exploded perspective view of the bearing carrier and internal components used with the guide of FIG. 2.
Figure 4:
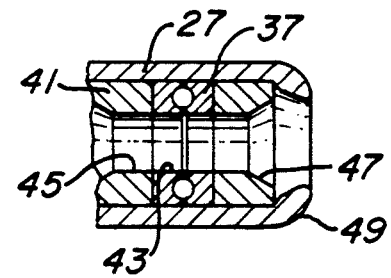
FIG. 4 is a vertical sectional view of a portion of the bearing carrier and bearing as illustrated in FIG. 3, shown assembled.

Referring to FIG. 3, bearing carrier 27 houses two bearings 37, 39. Each bearing 37, 39 has a pair of spacers 41, on each side. As can be seen also in FIG. 4, each bearing 37, 39 has a hole 43 extending through it. Hole 43 is only slightly greater in diameter than shank 17. This allows guide 23 to move axially along the shank 17. Each bearing 37, 39 has an outer race, which remains stationary, and an inner race which rotates with the shank 17.

Each spacer 41 also has a hole 45 that is coaxial with hole 43 in bearings 37, 39. Hole 45 has a flared section 47 on one side of each spacer 41. The flared sections 47 face away from the bearing 37 or 39 which is sandwiched between the spacers 41. This facilitates the entry of shank 17. Also, the ends 49 of bearing carrier 27 are rolled over once the bearings 37, 39 and spacers 41 have been inserted within.

In operation, the apparatus shown is for use in removing a prosthesis 51 from a bone 53. Prosthesis 51 may be of a variety of devices that have been previously inserted into a hole formed in bone 53 and secured by adhesive and also by bone growth to prosthesis 51. In the embodiment shown, prosthesis 5 is a porous coated member secured within a hole by bone growth in a femur portion of the hip joint.

The surgeon will initially insert shank 17 through bearing carrier 27. If tip 19 is enlarged relative to shank 17, the surgeon will necessarily insert the upper end opposite tip 19. The surgeon connects the shank 17 to the collet (not shown) of motor 11 in a conventional manner. The surgeon will grasp handle 25 in the other hand. The surgeon turns on motor 11 through a valve (not shown) to supply air pressure through hose 13. This will cause the shank 17 to rotate at a high speed.

The surgeon will place tip 19 at the perimeter of prosthesis 51 to begin dissecting a thin layer between prosthesis 51 and bone 53. The surgeon will move tip 19 around prosthesis 51 counterclockwise, which is opposite to the normal direction of rotation of shank 17. The surgeon will gradually deepen the dissected area until prosthesis 51 can be loosened from bone 53. The shank 17 will flex laterally to accommodate the irregular exterior of the prosthesis 51.

The invention has significant advantages. It allows a prosthesis to be resected from an imbedded engagement in a bone without the use of a osteotome. This avoids splintering.

While the invention has been shown in only one of its forms, it should be apparent to those skilled in the art that it is not so limited but is susceptible to various changes without departing from the scope of the invention.

We claim:

1. An apparatus for use with a rotary motor for removing a prosthesis from an embedded engagement within a bone, comprising in combination:
   a cutting tool having a cutting tip and an elongated flexible shank for connection to and being rotated by the motor;
   a guide having a hole therethrough which rotatably receives the shank of the cutting tool, the guide having a handle extending laterally from the shank and configured to be gripped by a hand of the user for guiding the cutting tool around the perimeter of the prosthesis to dissect a thin layer between the prosthesis and the bone to release the prosthesis from the bone; and
   wherein the guide has a bearing mounted thereto, the hole for the shank extending through the bearing.

2. An apparatus for removing a prosthesis from an embedded engagement within a bone with the use of a rotary motor, comprising in combination:
   a cutting tool having a cutting tip and an elongated shank for connection to and rotation by the motor, the shank having a diameter and length selected so as to allow significant lateral flexing;
   a handle configured to gripped by a hand of the user; and
   a bearing having a hole therethrough which receives the shank of the cutting tool, the bearing being mounted to the handle so that the handle extends laterally from the shank of the cutting tool, the 1 bearing allowing the handle to be moved axially along the shank of the cutting tool;
   wherein the user will move the motor and the handle to guide the cutting tool around the perimeter of the prosthesis to dissect a thin layer between the prosthesis and the bone to release the prosthesis from the bone.

3. The apparatus according to claim 2 further comprising:
   a bearing carrier, the bearing being mounted within the bearing carrier; and
   mounting means for releasably mounting the bearing carrier to the handle, so as to allow the bearing carrier to be removed from the handle for replacement.

4. An apparatus for removing a prosthesis from an embedded engagement within a bone, comprising in combination:
   a cutting tool having a cutting tip and an elongated shank which has a diameter and length selected so as to allow significant lateral flexing;
   motor means configured to be gripped by one hand of a user, the motor being connected to the cutting tool shank for providing rotational motion to the cutting tool;
   a handle configured to gripped by another hand of the user;
   a bearing carrier having a hole therethrough;
   mounting means for mounting the bearing carrier to one end of the handle and transverse to the handle; and
   a bearing mounted in the bearing carrier, having a hole therethrough which receives the shank of the cutting tool;
   wherein the user will move the motor means and the handle to guide the cutting tool around the perimeter of the prosthesis to dissect a thin layer between the prosthesis and the bone to release the prosthesis from the bone.

5. The apparatus according to claim 4 wherein the mounting means comprises:
   a pair of jaws on said one end of the handle, the bearing carrier being located within the jaws; and
   means for drawing the jaws together to grip the bearing carrier, and to release the jaws to allow the bearing carrier to be removed.

6. The apparatus according to claim 4 wherein the mounting means comprises:
   a pair of jaws on said one end of the handle, the bearing carrier being located within the jaws; and
   means, including a threaded screw extending between the jaws, for drawing the jaws together to grip the bearing carrier, and to release the jaws to allow the bearing carrier to be removed.

7. A method for removing a prosthesis from an embedded engagement within a bone, comprising:
   providing a cutting tool having a cutting tip and an elongated flexible shank;
   providing a guide with a handle and a hole therethrough;
   inserting the shank through the hole of the guide;
   connecting the shank of the cutting tool to a rotary motor;
   holding the motor with one hand and holding the handle with another hand; then
   rotating the cutting tool with the motor while guiding the cutting tool around the perimeter of the prosthesis with the guide, dissecting a thin layer between the prosthesis and the bone to release the prosthesis from the bone.

* * * * *